(12) United States Patent
Giudiceandrea

(10) Patent No.: US 8,306,761 B2
(45) Date of Patent: Nov. 6, 2012

(54) APPARATUS AND METHOD FOR IDENTIFYING THE POSITION OF DEFECTS IN BODIES, IN PARTICULAR IN WOODEN BODIES SUCH AS LOGS OR PLANKS

(75) Inventor: Federico Giudiceandrea, Bressanone (IT)

(73) Assignee: Microtec S.R.L., Bressanone (IT)

( * ) Notice: Subject to any disclaimer, the term of this patent is extended or adjusted under 35 U.S.C. 154(b) by 514 days.

(21) Appl. No.: 12/552,388

(22) Filed: Sep. 2, 2009

(65) Prior Publication Data

US 2010/0228500 A1   Sep. 9, 2010

(30) Foreign Application Priority Data

Sep. 18, 2008   (IT) .............................. VR2008A0104

(51) Int. Cl.
*G01B 5/30* (2006.01)
*G01B 15/06* (2006.01)
*G01J 1/42* (2006.01)

(52) U.S. Cl. ......... 702/40; 701/35; 701/189; 356/237.1; 378/58

(58) Field of Classification Search .................... 702/35, 702/40, 189; 356/237.1; 378/58
See application file for complete search history.

(56) References Cited

U.S. PATENT DOCUMENTS

| 5,394,342 A | 2/1995 | Poon |
| 6,157,698 A * | 12/2000 | Pietikainen et al. ............ 378/58 |
| 2004/0057551 A1 | 3/2004 | Skatter et al. |
| 2005/0190958 A1 | 9/2005 | Woods et al. |

FOREIGN PATENT DOCUMENTS

WO   WO 2004044566 A1 *   5/2004

OTHER PUBLICATIONS

Machine Translation of WO 2004044566.*

* cited by examiner

*Primary Examiner* — Andrew Schechter
*Assistant Examiner* — L. Anderson
(74) *Attorney, Agent, or Firm* — Pearne & Gordon LLP

(57) ABSTRACT

An apparatus for identifying the position of defects (100) in bodies (2), comprises feed means (3) for moving the body (3) along a feed direction (A), an emitter (5) designed to direct towards the body (2) a plurality of beams (6', 6", 6''') of electromagnetic radiation lying in lying planes (P1, P2, P3) set at different angles to each other, and transversal to the feed direction (A), and a plurality of sensors (8', 8", 8''') each facing the emitter (5) for receiving a respective beam (6', 6", 6''') after the beam (6', 6", 6''') has passed through the body (2). The lying planes (P1, P2, P3) are positioned one after another along the feed direction (A), allowing each portion of the body (2) to be struck by successive beams (6', 6", 6''') as the body (2) is fed forward. A corresponding method is also claimed.

15 Claims, 4 Drawing Sheets

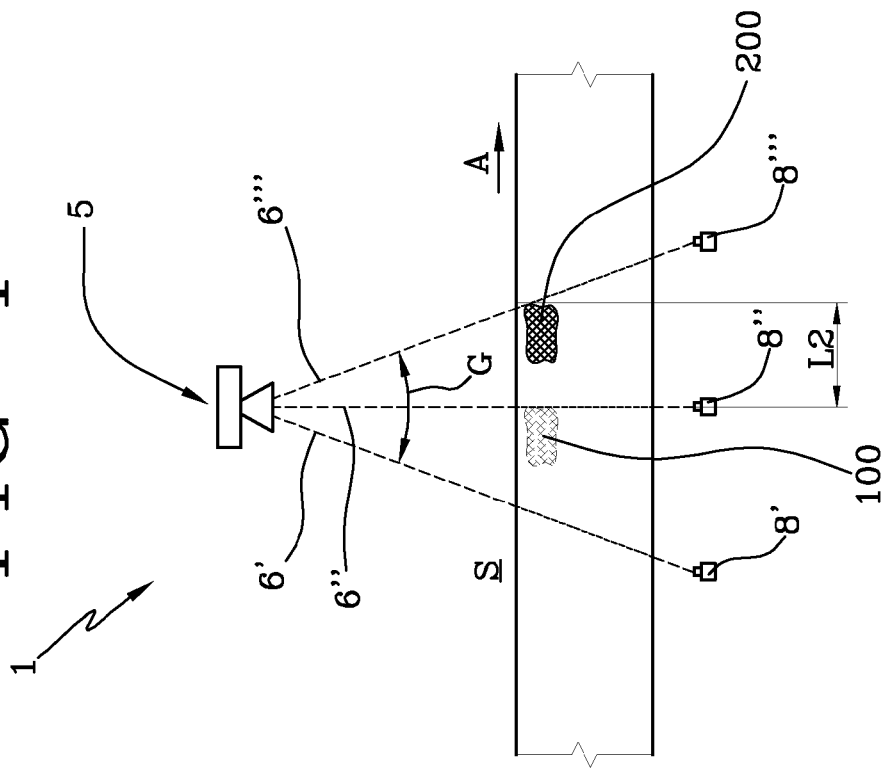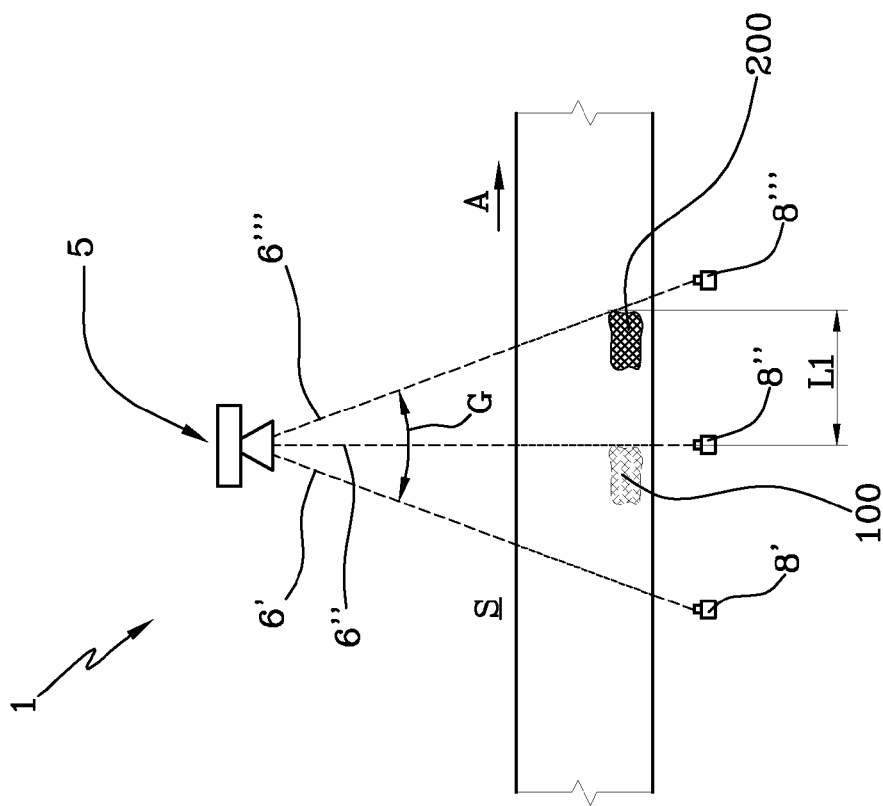

APPARATUS AND METHOD FOR IDENTIFYING THE POSITION OF DEFECTS IN BODIES, IN PARTICULAR IN WOODEN BODIES SUCH AS LOGS OR PLANKS

The present invention relates to an apparatus and a method for identifying the position of defects, such as knots, cracks or cavities, in wooden bodies such as logs or planks.

The detection of the positioning of defects in wooden logs or planks using suitable detection apparatuses is currently known. A first type of apparatus comprises two electromagnetic radiation emitters placed at a right angle to each other (usually one horizontal and one vertical) and lying in a plane which is perpendicular to a longitudinal axis of the log or plank, and also comprises two sensors positioned in such a way that each sensor receives the radiation emitted by one of the two emitters after it has passed through the wood.

A second type of detection apparatus comprises a single emitter and a plurality of sensors aligned along a direction perpendicular to the longitudinal axis of the wooden log or plank (said longitudinal axis usually coincides with a log or plank feed direction) for detecting the intensity of the radiation emitted by the emitter after it has passed through the wood. The emitter generates a beam of electromagnetic radiation with a diverging shape, that is to say, its size increasing from the emitter towards the sensors, thus allowing the radiation emitted to cover all of the sensors. The analysis of the intensity of the radiation detected by each sensor allows identification of which sensors encountered an abnormal intensity and, therefore, the position where the defect in the wood is located.

A third type of detection apparatus comprises a portal through which the log or plank to be analysed is passed. On the portal, which is positioned perpendicularly to the longitudinal axis of the log or plank, there are two emitters generating respective diverging beams. The emitters are set at an angle to each other, so that the same points of the log or plank are struck from two different angles and therefore the defect is "observed" form two different points. Again in this case, the sensors are aligned in a row positioned perpendicularly to the longitudinal axis of the log and are located below the portal.

However, the above-mentioned detection apparatuses have important disadvantages.

The apparatuses of the first type described above usually require the log or plank to be held stationary during the detection step, having a significant negative impact on the productivity of the plants in which such apparatuses are included. Moreover, the apparatuses of the first type require the use of two emitters which, as is well known, are amongst the most expensive components of a detection plant and therefore have a negative impact on plant production costs.

Detection apparatuses of the second type only have one emitter, but the information that it can provide is not sufficient to correctly identify the position in space of defects in the log or plank detected. Each sensor measures an intensity of radiation received and, if abnormal values are measured, it means that there is a defect in the wood between the emitter and that sensor. However, apparatuses of the second type cannot provide any information about the distance separating the defect from the emitter or from the sensor, since whatever the distance between the defect and the emitter or the sensor along a line linking them, the intensity detected by the sensor would be the same.

Apparatuses of the third type, similarly to those of the first type, have the disadvantage of requiring the use of two emitters, consequently increasing plant costs.

In this context, the technical purpose of the present invention is to provide an apparatus and a method for identifying the position of defects in bodies, in particular in wooden bodies such as logs or planks, which overcomes the above-mentioned disadvantages.

Within the scope of the technical purpose, the present invention has for an aim to provide an apparatus and a method for identifying the position of defects in bodies, in particular in wooden bodies such as logs or planks, which allows precise identification of the three-dimensional position of any defects whilst at the same time keeping plant costs down.

The technical purpose indicated and the aim specified are substantially achieved by an apparatus and a method for identifying the position of defects in bodies, in particular in wooden bodies such as logs or planks, comprising the technical features respectively described in claims 1 and 8 and in one or more of the claims dependent on them.

Further features and advantages of the present invention are more apparent from the non-limiting description which follows of a preferred, non-limiting embodiment of an apparatus and a method for identifying the position of defects in bodies, in particular in wooden bodies such as logs or planks, illustrated in the accompanying drawings, in which:

FIGS. 3 and 4 are schematic cross-sections of the apparatus of FIG. 2 according to different operating situations.

Figure 1:
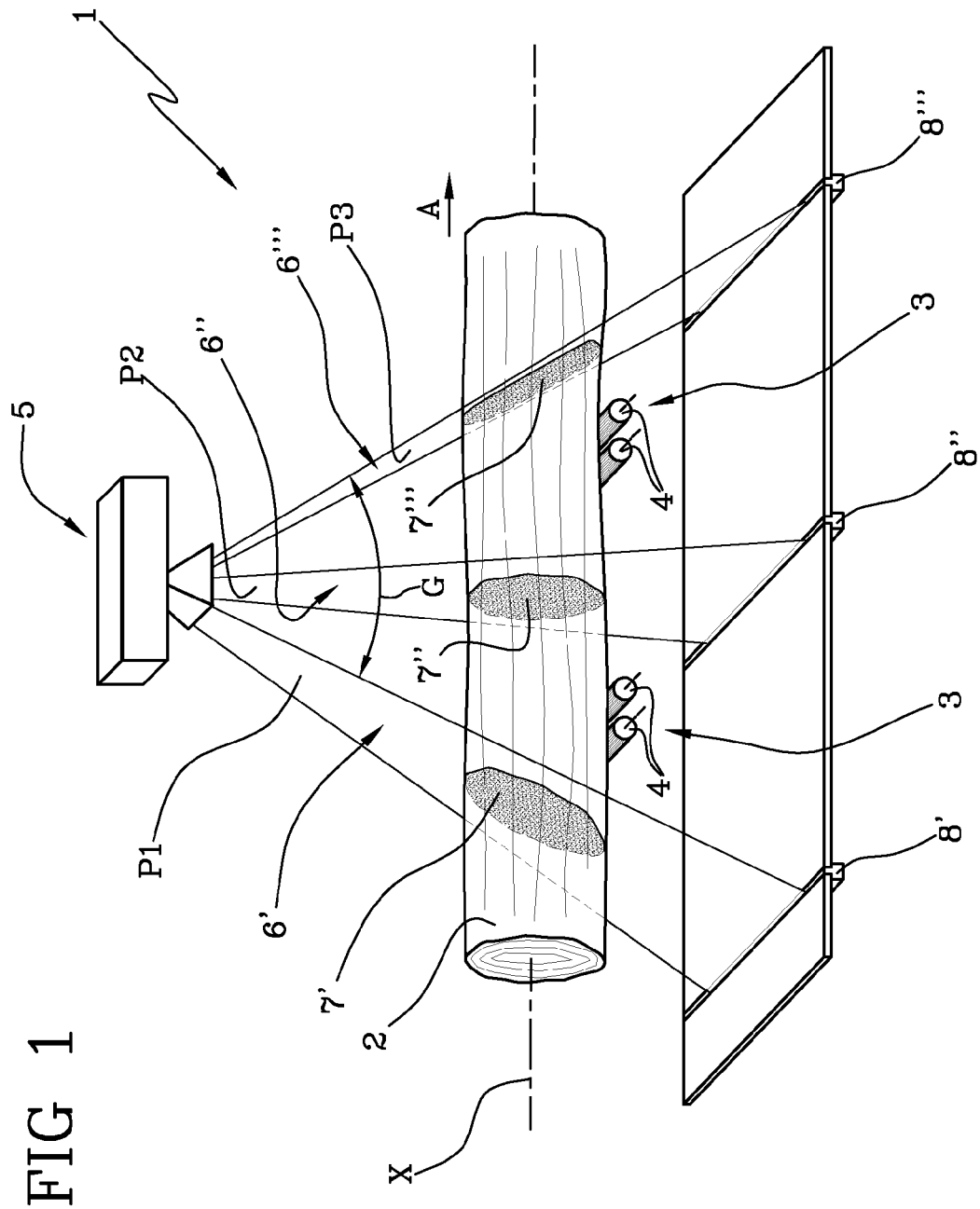
FIG. 1 is a schematic perspective view of the apparatus according to the present invention during a log analysis step.

With reference to the accompanying drawings, the numeral 1 denotes as a whole an apparatus for identifying the position of defects, such as knots, cracks or cavities, in bodies 2, in particular in wooden bodies 2 such as logs or planks. For example, FIG. 1 shows the apparatus 1 while it is acting on a body 2 in the form of a log, whilst in FIG. 2 the body 2 analysed is a wooden plank.

The apparatus 1 comprises body 2 feed means 3 for moving the body 2 along a feed direction "A" which is preferably horizontal. The feed means 3 comprise a plurality of rollers 4 connected to motor means, not illustrated, for pulling the body 2 along the feed direction "A". According to FIGS. 1 and 2, the feed direction "A" coincides with a main direction of extension X of the body 2.

The apparatus 1 also comprises an emitter 5 for emitting a plurality of beams 6', 6", 6'" of electromagnetic radiation. According to a preferred embodiment of the apparatus 1, the emitter 5 is an X-ray emitter. The beams 6', 6", 6'" lie in respective lying planes "P1", "P2'", "P3" extending from the emitter 5 and intersecting the body 2 which is opposite the emitter 5. The accompanying drawings show three beams 6', 6", 6'" for simplicity, however, other embodiments (not illustrated) are possible in which the emitter 5 is of the type designed to emit a larger number of beams, for example five, which in any event have the same properties as the three beams 6', 6", 6'".

Figure 2:
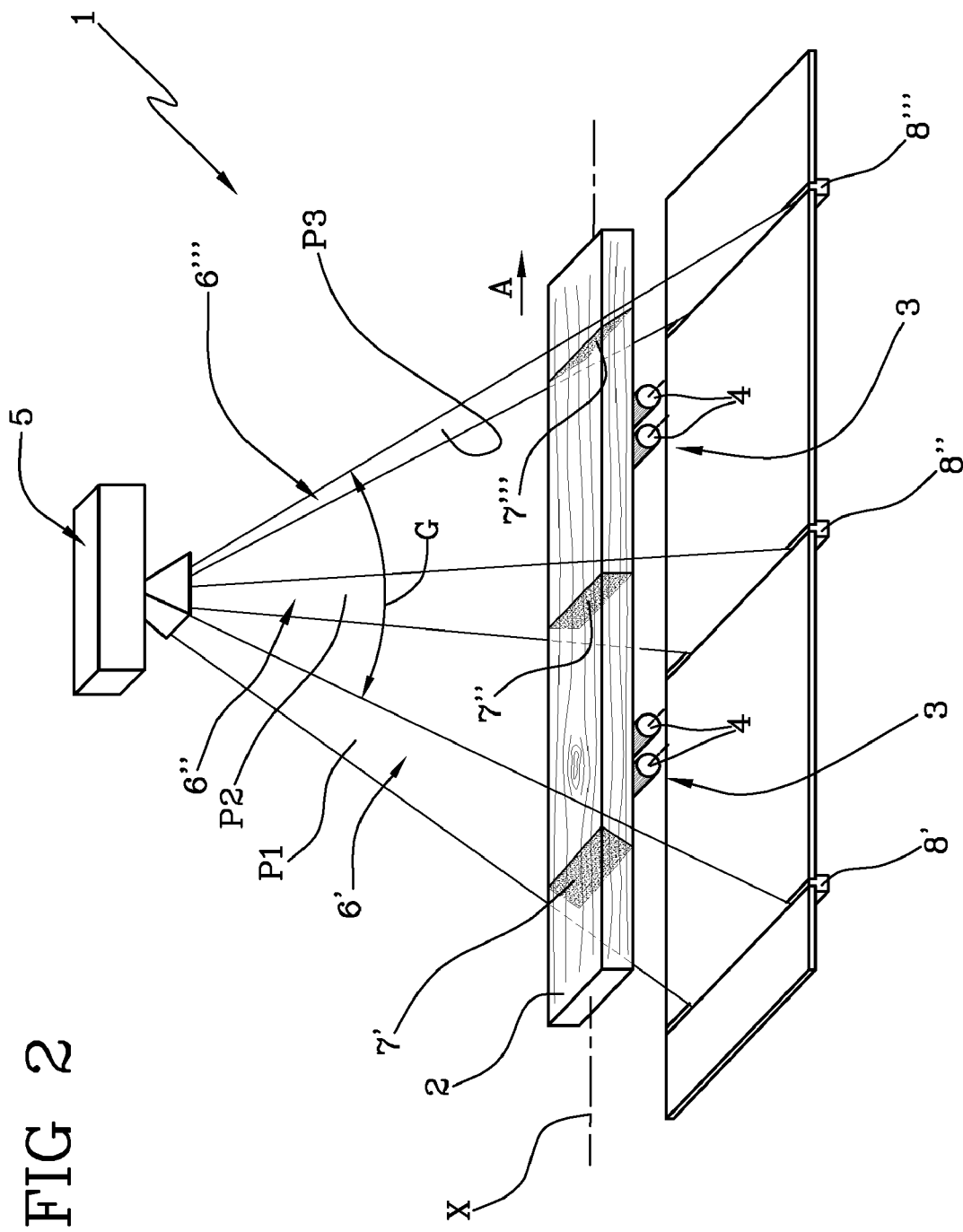
FIG. 2 is a schematic perspective view of the apparatus according to the present invention during a wooden plank analysis step.

According to the views in FIGS. 1 and 2, the emitter 5 is of the type able to generate beams 6', 6", 6'" according to respective lying planes "P1", "P2'", "P3" which are set at different angles to the feed direction "A". In other words, each of the lying planes "P1", "P2'", "P3" is set at a different angle relative to the other lying planes "P1", "P2'", "P3" for intersecting the body 2 both at different points of the body 2 and according to different directions. This means that the emitter 5 generates a plurality of beams 6', 6", 6'" diverging from each other away from the emitter 5 towards the body 2.

Each beam 6', 6", 6'" is preferably sized so that it strikes an entire transversal dimension of the body 2, said transversal dimension being perpendicular to the feed direction "A", in particular horizontal.

In the views in FIG. 1 or FIG. 2, the central lying plane 6" is substantially perpendicular to the feed direction "A", more precisely it is vertical. The other lying planes "P1", "P3" are set at an angle "G" to each other, forming a maximum flare angle for the emitter 5 electromagnetic emission. The angle "G" is preferably less than or equal to 90 degrees.

FIGS. 1 and 2 show, labelled 7', 7", 7'", the cross-sections of the body 2 identified by the intersection between the beams 6', 6", 6'" and the body 2. Said cross-sections 7', 7", 7'" are highlighted with dense background to highlight the different angles of the cross-sections 7', 7", 7'" caused by the different angles of the lying planes "P1", "P2'", "P3".

With reference to the accompanying drawings, the emitter 5 is positioned above the body 2 to be analysed. The apparatus 1 also comprises, on the opposite side of the body 2 relative to the emitter 5, that is to say, below the body 2, a plurality of sensors 8', 8", 8'" whose number is preferably the same as the number of beams 6', 6", 6'". Each sensor 8', 8", 8'" is designed to receive a respective beam 6', 6", 6'" of electromagnetic radiation after the beam 6', 6", 6'" has passed through the body 2. In more detail, each sensor 8', 8", 8'" can measure a residual intensity of the respective beam 6', 6", 6'" to identify how much energy the beam 6', 6", 6'" lost as it passed through the body 2. The analysis of the energy absorbed by the body 2 in each of the cross-sections 7', 7", 7'" allows evaluation of the existence of a defect in one or more of the cross-sections 7', 7", 7'", since the presence of defects distorts the energy absorption values, making them greater than or less than an expected normal value, characteristic of wood which is free of defects.

The apparatus 1 also comprises a processing unit, not illustrated, connected to the sensors 8', 8", 8'" and preferably also to the emitter 5 for receiving the intensity values of the beams 6', 6", 6'" emitted by the emitter 5 and detected by the sensors 8', 8", 8'". The processing unit can also store said data and associate it with a relative moment in time in which it was detected, allowing subsequent processing of the data, even complex processing, as described below.

FIGS. 3 and 4 help to explain the operating principle of the apparatus 1 described above.

First, it is assumed that in the body 2 there is a defect, labelled 100, whose existence is not known. The body 2 is then conveyed, by the feed means 3, through a space "S" between the emitter 5 and the sensors 8', 8", 8'" and is fed along the feed direction "A". The body 2 is fed with a known feed speed which is preferably kept constant at least during an entire body 2 detection step.

During body 2 feed, the defect 100 encounters, at successive moments, each of the beams 6, 6", 6'" of electromagnetic radiation. FIG. 3 shows a situation in which the defect 100 is located in a lower portion of the body 2, and shows the moment when the defect 100 encounters the central beam 6". The defect 100 is illustrated with a light line, whilst again in FIG. 3 the same defect is labelled 200 at the moment when it reaches the last beam 6'".

Each sensor 8', 8", 8'" detects a continuous succession of residual intensity values of each beam 6', 6", 6'" which emerges from the body 2. In other words, each sensor 8', 8", 8'" detects a succession of residual intensity values of each beam 6', 6", 6'" at moments which are close together, so as to detect, with predetermined precision, when a defect 100 is close to the respective beam 6', 6", 6'" detected.

Since at the moment when a defect encounters a beam of electromagnetic radiation it modifies a beam energy absorption which is instantaneously detected by the sensor, which sends a corresponding signal to the processing unit, the processing unit is always able to recognise whether or not at a predetermined moment a defect 100 is passing through one of the beams. Therefore, at the moment when the defect 100 encounters the central beam 6", the respective central sensor 8" detects a residual intensity value in the beam 6" detected. The processing unit receives from the sensor 8" a signal identifying the abnormal energy absorption and, therefore, identifies the existence of a defect 100 passing through the central beam 6".

As the body 2 is fed forwards, the defect 100 reaches the last beam 6'", reaching the configuration shown in FIG. 3 in which the defect is labelled 200 and shown with a thick line. In said configuration, the last sensor 8'" detects an abnormal residual intensity value in the last beam 6'" and this is associated with an abnormal energy absorption in that beam 6'" and, therefore, linked to a defect 200 passing through the last beam 6'".

After measuring the time interval between the indications of the presence of a defect from the sensors 8", 8'" and knowing the constant feed speed of the body 2, the processing unit can identify a distance "L1" travelled by the defect 100 between the central beam 6" and the last beam 6'". Once said distance travelled "L1" information has been obtained, and knowing the geometry of the planes "P1", "P2'", "P3" in which the beams 6', 6", 6'" lie, the processing unit can unambiguously evaluate the vertical position of the defect 100, that is to say, the position of the defect 100 along a direction linking the emitter 5 with one of the sensors 8', 8", 8'".

In other words, the information detected regarding the residual intensity of each beam 6', 6", 6'" is processed and combined to identify the positioning in space of the defect 100 at a predetermined moment and, based on the knowledge of the body 2 feed speed and therefore the position of the body 2, to identify the position in space of the defect 100 inside the body 2.

The above is better illustrated by comparing FIGS. 3 and 4, in which it may be seen how different distance travelled values ("L1", "L2") identify different vertical positions of the defect 100, the geometry of the beams 6', 6", 6'" being equal. In particular, FIG. 4 shows a defect 100 which is positioned higher up than the defect 100 of FIG. 3. Due to the configuration of the beams 6', 6", 6'" diverging from top to bottom, the defect 100 of FIG. 4 must travel a distance "L2" which is less than the distance "L1" that must be travelled by the defect of 100 FIG. 3, in order to get from the central beam 6" to the last beam 6'". The processing unit uses this information, starting (directly or implicitly) with identification of the distance travelled "L1", "L2" to unambiguously evaluate the vertical position of the defect 100.

Preferably, each of the sensors 8', 8", 8'" comprises a plurality of sensitive elements (not illustrated) which are aligned along a direction perpendicular to the body 2 direction of feed "A", that is to say, perpendicular to the views of FIGS. 3 and 4. When analysing the intensity of the radiation detected by each sensitive element, this allows identification of the position of the defect 100 in a horizontal plane.

Detection of the position of the defect 100 both in a vertical direction, or more generally in a direction linking the emitter 5 with one of the sensors 8', 8", 8'", and in a horizontal plane, that is to say, in a plane transversal to said linking direction, allows the three-dimensional positioning of the defect 100 inside the body 2 to be obtained.

Figure 5:
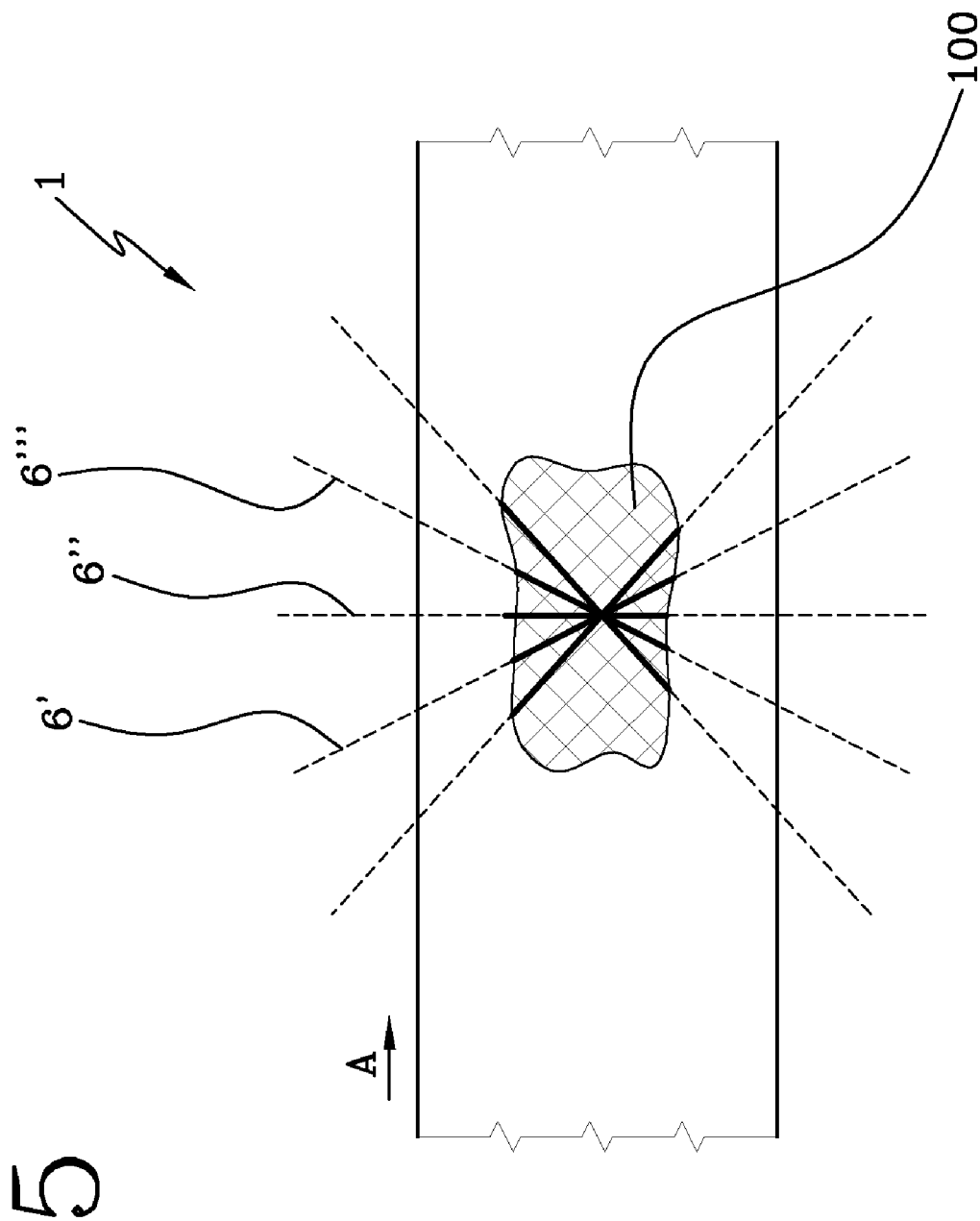
FIG. 5 is a cross-section of a numerical reconstruction of a portion of a wooden body according to the method disclosed by the present invention.

An alternative application of the apparatus 1 according to the present invention also allows precise estimation of an outer profile of the defect 100. Each point of the body 2 is struck one after another by each of the beams 6', 6", 6''' in three different directions, and for each of the three beams 6', 6", 6''' the energy absorption is measured by means of the respective sensor 8', 8", 8'''. By bringing together the three detections relating to the same point of the body 2 (measured at different moments, therefore stored in the memory and selectively retrieved by the processing unit), and repeating said operations for a grid of points of the body 2, it is possible to use interpolation to obtain an estimate of the outer profile of the defect 100. Said estimate is more precise the greater the number of different directions in which the detections are carried out. FIG. 5 shows an example of a detection of a defect 100 using five detections obtained with five beams of electromagnetic radiation, in which the thicker lines are segments whose length is linked, for example proportionally, to an absorption value detected by the sensors. Said detection is then repeated for a grid of body 2 points adjacent to each other so as to precisely identify the outer profile of the defect 100.

The present invention achieves the preset aim, overcoming the disadvantages of the prior art.

The apparatus according to the invention has only one electromagnetic radiation emitter, but comprises a plurality of sensors operating in conjunction with it. Since the sensors are much less expensive than an electromagnetic radiation emitter, and in particular an X-ray emitter, the apparatus is obviously significantly less expensive than other, prior art apparatuses.

Moreover, the method according to the invention allows, starting with the emission of beams of electromagnetic radiation from a single emitter, precise and reliable identification of the position in space of any defects present in the bodies detected. This also allows an estimate of the trend of the outer profile of the defect.

Moreover, if the emitter were of the type able to generate more than three beams of electromagnetic radiation (consider even a very high number), it would be possible to very precisely identify both the position of defects which are superposed and/or located in positions close to each other, which would normally tend to blend with one another, also identifying the trend of the outer profile of said defects.

Finally, the possibility of analysing the body while it is fed forward allows high productivity, since there are no periods of time during which the body is stopped at the apparatus.

The invention claimed is:

1. An apparatus for identifying the position of defects (100) in bodies (2), in particular in wooden bodies such as logs or planks, comprising:
   an emitter (5) which can be placed so that it faces a body (2) for directing a plurality of beams (6', 6", 6''') of electromagnetic radiation towards the body (2), each of the beams (6', 6", 6''') lying in a respective lying plane (P1, P2, P3);
   a plurality of sensors (8', 8", 8''') each of which is facing the emitter (5) for receiving one of the beams (6', 6", 6''') after the beam (6', 6", 6''') has passed through the body (2); the sensors (8', 8", 8''') and the emitter (5) between them delimiting a space (S) in which the body (2) is positioned;
   feed means (3) for moving the body (3) along a direction of feed (A) through the space (S); the apparatus being characterised in that the planes (P1, P2, P3) in which the beams (6', 6", 6''') lie are set at different angles to each other and are orientated transversally to the direction of feed (A), the lying planes (P1, P2, P3) being positioned one after another along the direction of feed (A) so that the same portion of the body (2) can be struck by successive beams (6', 6", 6''') as the body (2) is fed forward.

2. The apparatus according to claim 1, characterised in that the emitter (5) generates the beams (6', 6", 6''') according to a configuration diverging from the emitter (5) towards the sensors (8', 8", 8''').

3. The apparatus according to claim 1, characterised in that the emitter (5) generates the beams (6', 6", 6''') with a flare angle (G) which is less than or equal to 90 degrees, said flare angle (G) being measured between a first beam (6') and a last beam (6''') relative to the direction of feed (A).

4. The apparatus according to claim 1, characterised in that it comprises a single emitter (5).

5. The apparatus according to claim 1, characterised in that the sensors (8', 8", 8''') are positioned one after another along the direction of feed (A).

6. The apparatus according to claim 1, characterised in that each sensor (8', 8", 8''') comprises a plurality of sensitive elements which are aligned along a direction transversal to the direction of feed (A), for identifying the position of defects (100) along the transversal direction.

7. The apparatus according to claim 1, characterised in that it comprises a processing unit connected to the sensors (8', 8", 8''') for receiving from the sensors (8', 8", 8''') the intensity values of each of the beams (6', 6", 6''') detected, the processing unit also detecting a body (2) feed speed along the direction of feed (A).

8. A method for identifying the position of defects in bodies, in particular in wooden bodies such as logs or planks, comprising the following steps in the order in which they are listed:
   feeding a body (2) along a direction of feed (A);
   striking at least one portion of the body (2) with a plurality of beams (6', 6", 6''') of electromagnetic radiation, each beam (6', 6", 6''') lying in a respective lying plane (8', 8", 8''');
   detecting a residual intensity of each of the beams (6', 6", 6''') after they emerge from the body (2) for evaluating the energy absorbed by said portion of the body (2);
   identifying the position of a defect (100) present in the body (2);
   the method being characterised in that the step of striking at least part of the body (2) comprises a step of generating a plurality of beams (6', 6", 6''') lying in respective lying planes (8', 8", 8''') which are set at different angles to the direction of feed (A) in such a way that the beams (6', 6", 6''') pass through the portion of the body (2) at points located one after another along the direction of feed (A), the step of identifying the position of a defect (100) comprising a step of processing information about the beams (6', 6", 6''') which emerged from the body (2).

9. The method according to claim 8, characterised in that the step of striking at least one portion of the body (2) with a plurality of beams (6', 6", 6''') of electromagnetic radiation is carried out simultaneously with the step of feeding the body (2) along the direction of feed (A).

10. The method according to claim 8, characterised in that it comprises, after said steps, the further steps of:
   identifying moments in time when successive sensors (8', 8", 8''') detect the passage of the same defect (100) through the respective beam (6', 6", 6''') detected by each sensor (8', 8", 8''');

calculating distances (L1, L2) travelled by the defect (100) along the direction of feed (A) and corresponding to said moments in time;

identifying, based on said calculating step, a position of the defect (100) at least along a direction linking the emitter (5) with one of the sensors (8', 8", 8'").

11. The method according to claim 10, characterised in that it comprises another step of identifying the position of the defect (100) in a plane transversal to the direction linking the emitter (5) with one of the sensors (8', 8", 8'") for identifying, in conjunction with the position of the defect (100) along the direction linking the emitter (5) with the sensor (8', 8", 8'"), a position of the defect (100) in space relative to the body (2).

12. The method according to claim 10, characterised in that the step of identifying moments in time when successive sensors (8', 8", 8'") detect the passage of the same defect (100) comprises a step of comparing an intensity value for the beam (6', 6", 6'") arriving at each sensor (8', 8", 8'") with a relative expected value, the expected value relating to an intensity which can be measured in the absence of defects (100).

13. The method according to claim 8, characterised in that the step of detecting a residual intensity of each of the beams (6', 6", 6'") after they have emerged from the body (2) is carried out by detecting a continuous succession of intensity values of each beam (6', 6", 6'"), the step of identifying the position of a defect (100) comprising a step of sending the intensity values of each beam (6', 6", 6'") to a processing unit.

14. The method according to claim 8, characterised in that the step of striking said portion of the body (2) is carried out by striking an entire transversal dimension of said portion of the body (2), the transversal dimension being orientated in such a way that it is perpendicular to the direction of feed (A).

15. The method according to claim 8, characterised in that the step of feeding the body (2) along the direction of feed (A) is carried out by feeding the body (2) at a constant feed speed.

* * * * *